United States Patent [19]

Wuest et al.

[11] Patent Number: 4,851,525

[45] Date of Patent: Jul. 25, 1989

[54] CONVERSION OF ORGANOPHOSPHONIC ACIDS INTO THEIR SALTS USING INTENSE SHEAR

[75] Inventors: Willi Wuest, Ratingen; Hubert Harth, Duesseldorf; Dirk Springer, Haan; Franz Foerg, Langenfeld, all of Fed. Rep. of Germany

[73] Assignee: Henkel Kommanditgesellschaft auf Aktien, Duesseldorf, Fed. Rep. of Germany

[21] Appl. No.: 84,530

[22] Filed: Aug. 12, 1987

[30] Foreign Application Priority Data

Aug. 13, 1986 [DE] Fed. Rep. of Germany ....... 3627469

[51] Int. Cl.$^4$ .................... C07F 9/56; C07F 9/65; C07B 41/02
[52] U.S. Cl. ................. 540/542; 546/21; 548/412
[58] Field of Search ............ 540/542; 546/21; 548/412; 260/502.4 R

[56] References Cited

U.S. PATENT DOCUMENTS

| | | | |
|---|---|---|---|
| 3,941,772 | 3/1976 | Ploger et al. | 260/239 B |
| 3,969,295 | 7/1976 | Sunden | 524/556 |
| 3,988,443 | 10/1976 | Plöger et al. | 424/200 |

OTHER PUBLICATIONS

Chemical Engineer's Handbook, Robert H. Perry, Cecil H. Chilton, Fifth Edition, pp. 8-37-8-38, 8-55-8-56, 19-14-91-17, 19-21-19-23.
Chemical Engineer's Handbook, John H. Perry, Ph.D., Second Edition, pp. 1572-1574, 1941.

*Primary Examiner*—Mark L. Berch
*Attorney, Agent, or Firm*—Ernest G. Szoke; Wayne C. Jaeschke

[57] ABSTRACT

Process for the conversion of an organophosphonic acid of the formula

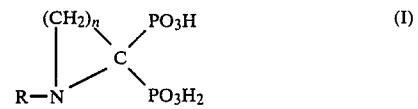

in which n=3-5 and R=H or $C_1$-$C_3$ alkyl, into an alkali metal or ammonium salt comprising reacting the moist filter cake which accumulates during the production of organophosphonic acids by known processes (water content 10 to 40% by weight) with anhydrous or concentrated aqueous alkali metal hydroxide or ammonia and exposing the paste formed, which has a water content of from 20 to 80% by weight, to intense shear forces in mixing, dispersing, or kneading units, water being removed from the paste under reduced pressure and with application of heat until the paste changes into a free-flowing powder.

8 Claims, No Drawings

CONVERSION OF ORGANOPHOSPHONIC ACIDS INTO THEIR SALTS USING INTENSE SHEAR

BACKGROUND OF THE INVENTION

1. Field of the Invention

This invention relates to a process for the conversion of azacycloalkane-2,2-diphosphonic acids into their alkali metal or ammonium salts, the salts being obtained in the form of freeflowing low-dust powders.

2. Statement of Related Art

In known processes for the neutralization of organophosphonic acids, the acids are combined in the form of aqueous solutions with aqueous solutions of alkali metal hydroxides or ammonia. The dilute aqueous solutions of the salts obtained in this way are unsuitable for use in this form, for example, in anhydrous or substantially anhydrous formulation. The transport of dilute aqueous solutions also involves considerable costs. Accordingly, the water present in the dilute aqueous solutions has to be removed, and this is very expensive in terms of energy requirements, e.g. utilizing spray drying or drying on rollers. Apart from their high energy demand, these drying processes have other disadvantages. In spray drying, very fine powders are formed, quantities of which become entrained due to the strong movement of air; and this can lead to serious losses. Where solutions are concentrated by evaporation or roller dryers, for example, coarse agglomerates are generally formed and have to be subsequently ground.

U.S. Pat. No. 3,941,772 and 3,988,443 disclose such acids and their salts, and their use as sequestering agents, e.g. in the treatment of certain disease states.

DESCRIPTION OF THE INVENTION

Other than in the operating examples, or where otherwise indicated, all numbers expressing quantities of ingredients or reaction conditions used herein are to be understood as modified in all instances by the term "about".

The disadvantages of known processes can be avoided by converting organophosphonic acids into their alkali metal or ammonium salts in accordance with the invention. The process of the invention is carried out with organophosphonic acids of the type obtained, for example, in accordance with German published application No. 23 43 196, and in particular to azacycloheptane-2, 2-diphosphonic acid, although it is also applicable to other organophosphonic acids having similar physical properties.

More specifically, the present invention relates to a process for the conversion of organophosphonic acids of the formula

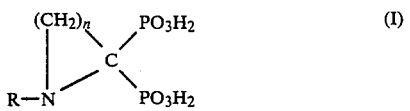

in which $n=$ an integer of from 3–5 and R is a hydrogen atom or a $C_1$–$C_3$ alkyl group, into their alkali metal or ammonium salts, comprising the steps of:

(a) reacting the crystalline organophosphonic acids in the form of the moist filter cake accumulating during their production (water content 10 to 40% by weight), e.g. according to the process described in U.S. Pat. No. 3,941,772, with the calculated quantity of alkali metal hydroxide or ammonia in anhydrous form or in concentrated aqueous solution and additional water, if any, which is needed to result in the formation of a paste having a water content of from 20 to 80% by weight, and preferably from 30 to 50% by weight, in the presence of intense shear forces in mixing, dispersing, or kneading units (neutralization step).

(b) removing water from the paste with application of heat and reduced pressure, and optionally with further application of shear forces in the mixing, dispersing or kneading units, until the paste changes into a freeflowing powder (drying step).

In the production of the organophonosphonic acids in accordance with U.S. Pat. No. 3,941,771/3,988,443, which are incorporated herein by reference, the acids are obtained in the form of moist crystalline masses (filter cakes) which typically have a water content of from 10 to 40% by weight. The quantity of alkali metal hydroxide or ammonia required for neutralization depends on whether the mono-, di-, tri-, or tetra-alkali metal salt or the mono-, di-, tri-, or tetra-ammonium salt of these tetrabasic acids is to be produced. The process of the invention is suitable for the production of any neutralization stage, i.e. the acidic, neutral, or basic salts. The alkali metal hydroxide or the ammonia may be introduced in anhydrous form or in the form of aqueous solutions. If anhydrous bases in solid form or gaseous ammonia is used, water should if necessary be additionally introduced in such a quantity that a paste having a water content of from 20 to 80% by weight, and preferably of from 30 to 50% by weight, is formed during the neutralization step. The additional introduction of water is unnecessary if the crystalline mass used already contains at least 20% by weight of water, although preferably at least 30% by weight of water.

The process of the invention is carried out in apparatus which can be heated, cooled, evacuated and which is equipped with powerful mixing and dispersing units which enable intense shear forces to be applied even to viscous pastes. Suitable apparatus for this purpose includes, for example, vessels incorporating a rotor-stator machine, mixers, and kneaders. Paddle dryers with built-in pinned disc mills and cutter mills have proven to be particularly successful.

During the mixing in of the alkali metal hydroxide or ammonia, the initially still moist crystalline mass changes into a viscous paste in which a uniform reaction resulting in the salt takes place in a short time under the influence of the intense shear forces of the mixing, dispersing, or kneading units. The reaction is exothermic and it may be necessary to keep the temperature of the product in the range of from 30° to 150° C., preferably from 50° to 100° C., by cooling. There is no need for cooling if, through particularly slow addition of the alkali metal hydroxide in relatively small batches, the reaction temperature does not exceed 100° C.

The drying of the paste after the neutralization step is carried out under reduced pressure with application of heat. For pressures below 500 mbar, heat is applied so that the product temperature is from about 50° to 100° C. Steam is continuously removed until the paste changes into a free-flowing powder under the effect of the mixing, dispersing, or kneading units. A dust-fine, substantially dehydrated crystalline organophosphonic acid salt can be obtained in this way. However, it is recommended to continue drying to a residual moisture content of from 8 to 12% by weight $H_2O$. A particularly readily soluble low-dust but freeflowing powder is obtained in this way.

The process according to the invention is illustrated but not limited by the following Example.

EXAMPLE

Azacycloheptane-2,2-diphosphonic acid disodium salt 150 kg crude, moist azacycloheptane-2,2-diphosphonic acid (water content 27% by weight, 425 moles of diphosphonic acid) were introduced into a paddle dryer with a built-in cutter mil. The mixer was then switched on and 67.7 kg of a 50% sodium hyrdoxide (846 moles) solution were sprayed on over a period of one hour. The temperature of the reaction mixture, which heats up spontaneously, is kept at 60° to 70° C. by external cooling.

After 30 minutes, the reaction jacket was heated to 150° C. and the internal pressure reduced to 160 mbar. Water evaporated and cooled the reactor contents to about 60° C. Toward the end of the water evaporation process, the temperature of the reactor contents rose to +70° C. while the pressure fell to 100 mbar.

After the heating had been switched off, the apparatus vented and the mixer turned off, a fine non-dusting crystal powder had formed in a quantity of 144 kg with a water content of 11% by weight.

We claim:

1. A process for the conversion of an organophosphonic acid of the formula

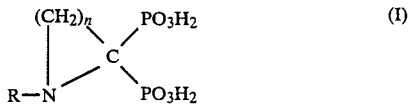

wherein n is an integer of from 3 to 5, and R is hydrogen or a $C_1$-$C_3$ alkyl group, into an alkali metal or ammonium salt, comprising the steps of:

(a) reacting a moist filter cake of an organophosphonic acid of formula I having a water content of from about 10 to about 40% by weight, in the presence of intense shear forces, with a predetermined quantity of an alkali metal hydroxide or ammonia in anhydrous form or in the form of a concentrated aqueous solution to form a paste having a water content of from about 20 to about 80% by weight, and (b) while continuing the intense shear forces of step (a), applying to the paste reduced pressure and heat until the paste is converted into a free-flowing powder.

2. The process of claim 1 wherein the intense shear forces in steps (a) and (b) are applied by mixing.

3. The process of claim 1 wherein steps (a) and (b) are both carried out at a temperature of from about 50° to about 100° C.

4. The process of claim 1 wherein in step (a) the paste has a water content of from about 30 to about 50% by weight.

5. The process of claim 1 wherein in step (a) the temperature is maintained in the range of from about 30° to about 150° C.

6. The process of claim 3 wherein in step (a) the temperature is maintained by controlling the rate of addition of the alkali metal hydroxide or ammonia.

7. The process of claim 1 wherein step (b) is carried out until the free-flowing powder has a residual water content of from about 8 to about 12% by weight.

8. The process of claim 1 wherein the process is carried out in a paddle dryer having a built-in pinned disc or cutter mills.

* * * * *